United States Patent [19]
Perry et al.

[11] Patent Number: 5,651,773
[45] Date of Patent: Jul. 29, 1997

[54] SKIN PROTECTOR FOR ULTRASONIC-ASSISTED LIPOSUCTION AND ACCESSORIES

[76] Inventors: Larry C. Perry, 3333 Country Ridge Dr., Antioch, Tenn. 37013; G. Patrick Maxwell, 4416 Gerald Pl., Nashville, Tenn. 37205

[21] Appl. No.: 588,615

[22] Filed: Jan. 19, 1996

[51] Int. Cl.⁶ .................................................. A61M 5/32
[52] U.S. Cl. ......................... 604/174; 604/19; 604/283; 604/905
[58] Field of Search ........................ 604/19, 21, 174, 604/175, 164, 264, 902, 283, 905, 268, 273, 274, 104

[56] References Cited

U.S. PATENT DOCUMENTS

| | | | |
|---|---|---|---|
| 3,876,234 | 4/1975 | Harms | 285/38 |
| 4,318,401 | 3/1982 | Zimmerman | 128/214 |
| 4,596,552 | 6/1986 | DeVries | 604/44 |
| 5,176,649 | 1/1993 | Wakabayashi | 604/164 |
| 5,213,567 | 5/1993 | Masaki | 604/19 |
| 5,364,367 | 11/1994 | Banks et al. | 604/174 |

*Primary Examiner*—John D. Yasko
*Assistant Examiner*—Cris L. Rodriguez
*Attorney, Agent, or Firm*—Paul M. Craig, Jr.

[57] ABSTRACT

A skin protector and accessories for protection of the skin incision during ultrasonic-assisted liposuction from thermal and frictional abrasion includes a skin protector made from sterilizable material which resists deformation and incorporates an outer configuration to assist in maintaining in situ positioning of the skin protector during operative procedure. An introducer member for blunt dissection of a tunnel is provided to allow easy insertion of the skin protector and ultrasonic probe. A driver member for dilatation of the skin incision, and for insertion and removal of the skin protector is also provided to assist in the use of the skin protector, properly speaking.

21 Claims, 3 Drawing Sheets

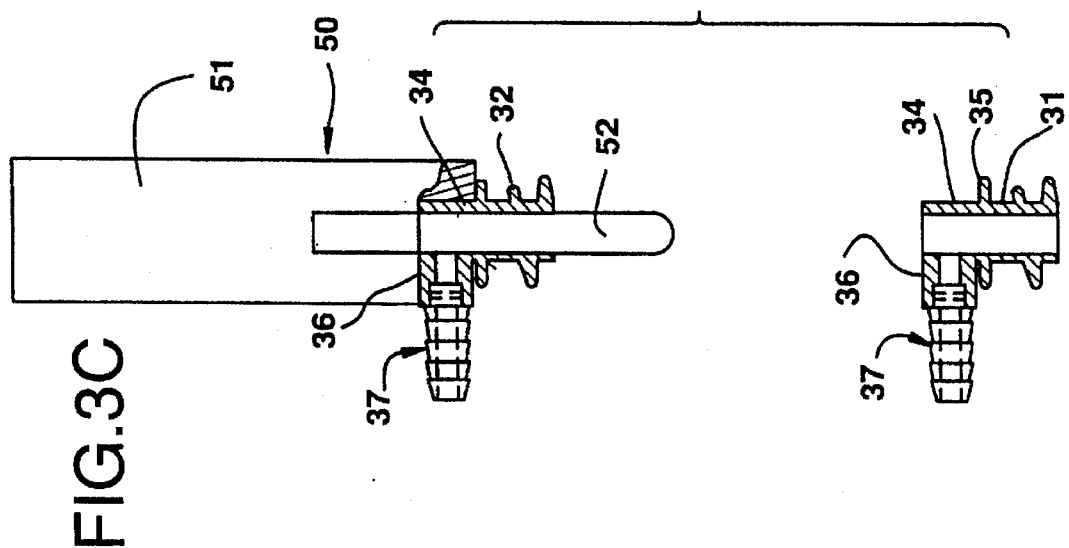
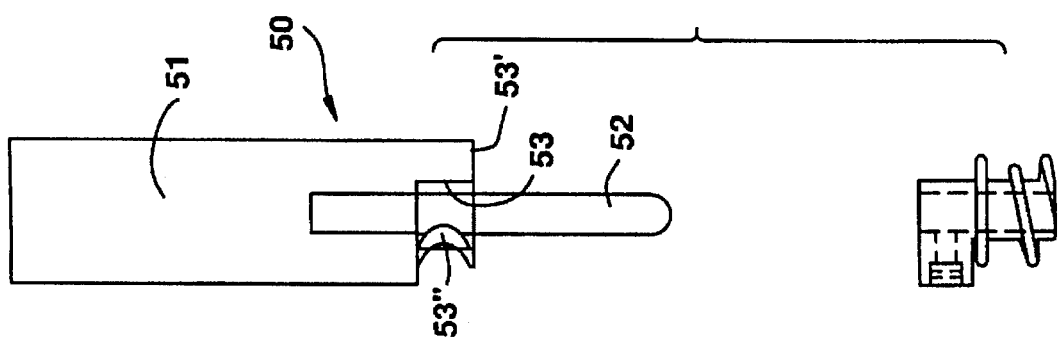
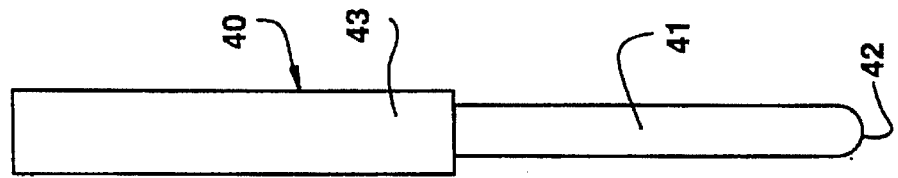

SKIN PROTECTOR FOR ULTRASONIC-ASSISTED LIPOSUCTION AND ACCESSORIES

FIELD OF INVENTION

This invention relates to a skin protector and accessories, especially for use in ultrasonic-assisted liposuction.

BACKGROUND OF THE INVENTION

The surgical treatment of lipodystrophy using suction-assisted lipectomy has evolved rather dramatically over the past fifteen years. It was first introduced in Europe in the late 1970's and began to attract attention in the United States in the early 1980's. It was first practiced using sharp curettage with secondary suction and later evolved to a more controlled vacuum suctioning of fat using large blunt cannulas. Eventually smaller specialized cannulas and various suction techniques were introduced allowing more selective and controlled removal of adipose tissue. More recently, the introduction of the tumescent technique has reduced fluid and electrolyte shifts allowing larger volumes of fat to be removed.

The most recent "advance" in the field of body contouring is the introduction of ultrasonic-assisted liposuction. The application of ultrasonic energy to adipose tissue "emulsifies" the fat by cellular cavitation causing the release of fatty acids into the intercellular spaces. The combination of the free fatty acids, normal interstitial fluid and the tumescent fluid forms a stable fatty emulsion which can then be extracted from the subcutaneous space using small suction cannulas. Proponents of this technique contend that it is a safe method of body contouring and that it has a number of advantages over traditional liposuction techniques. It is reported to allow greater suction volumes per patient with significantly less blood loss, better control of contour and physical alteration of the over skin.

The equipment and instrumentation used for ultrasonic-assisted liposuction generally consist of an electrical signal generator, a hand-piece unit including a piezoelectric crystal to transform the electrical energy from the generator into mechanical vibration and a solid or hollow probe which amplifies the longitudinal motion and provides the direct surface area (tip) for generating cellular cavitation. Various probes have been designed in an attempt to facilitate the evacuation of aspirate during the application of ultrasonic energy. In addition, some probes allow for the infusion of fluid within, or around the probe, providing a cooling mechanism for the probe-soft tissue interface.

The surgical procedure requires a full thickness linear skin incision. The ultrasonic probe or cannula is delivered through the skin incision. The probe is continuously placed in motion by the surgeon during the application of ultrasonic energy as research has demonstrated static positioning may potentially increase the risk of thermal abrasion.

SUMMARY OF THE INVENTION

A principal object of the present invention is a skin protector which protects the skin in the area of the incision especially during ultrasonic-assisted liposuction from both thermal and frictional abrasion and which decreases the amount of time required for removal of aspirate by providing an additional source of vacuum at the incisional site.

The skin protector and accessories of this invention include a skin protector made from gas (ETO) or steam sterilizable material which resists deformation and incorporates an outer configuration to aid in maintaining positioning in situ during the operative procedure, an introducer for blunt dissection of a tunnel to allow insertion of the skin protector and ultrasonic probe and to serve also as a guide in the creation of an appropriate sized skin incision, when applicable, and a driver member for dilatation of the skin incision and for insertion and removal of the skin protector.

In a preferred embodiment, the skin protector is provided with a lower part, adjoined by a flange-like part intended to rest on the outer surface of the skin, which is followed by an upper part provided with a stub-like connecting portion for the connection of a connecting nipple by way of a swivel joint to enable connection with a suction line that is freely rotatable relative to the skin of the patient. The lower part is preferably provided with some anchoring means to minimize the likelihood of inadvertent removal or withdrawal of the skin protector out of the incision.

BRIEF DESCRIPTION OF THE DRAWINGS

These and other objections, features and advantages of the present invention will become more apparent from the following description when taken in connection with the accompanying drawing which shows, for purposes of illustration only, a preferred embodiment of this invention, and wherein:

FIG. 3A is an elevational view of an introducer member for use with the skin protector of this invention;

FIG. 3B is a driver member for use with the skin protector of this invention, also showing the skin protector body and nipple disassembled from one another; and FIG. 3C is an elevational view, partly in cross section, illustrating the assembled skin protector and nipple with the installed driver member.

DETAILED DESCRIPTION OF THE DRAWINGS

Figure 1:
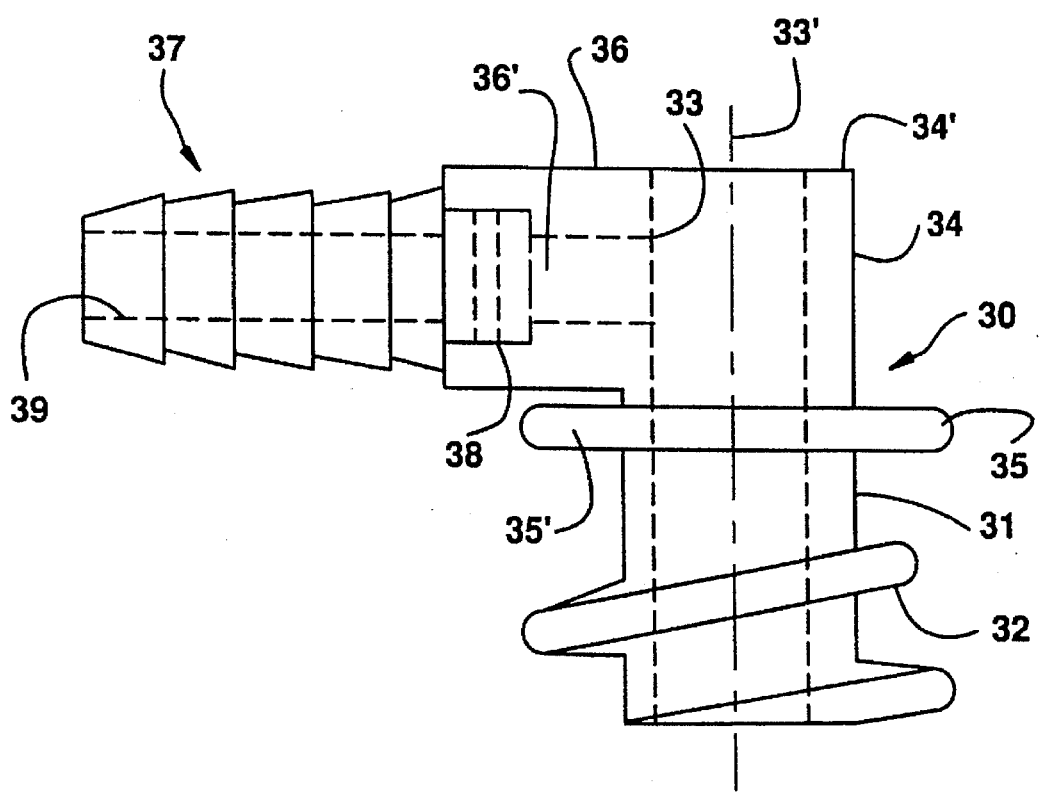
FIG. 1 is an elevational view of one embodiment of a skin protector of this invention, on an enlarged scale.
Figure 2A:
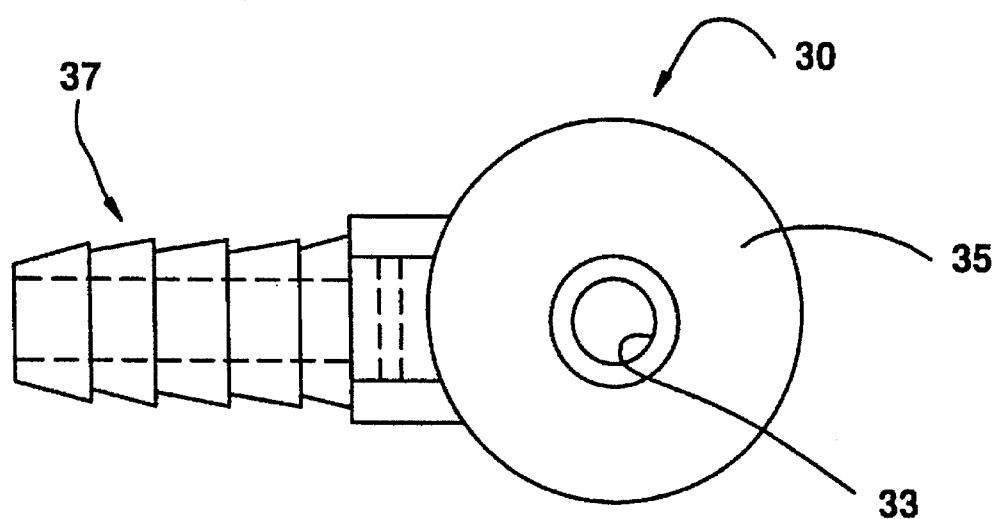
FIG. 2A is an elevational view, similar to FIG. 1 with an indication of the dimensions thereof.
Figure 2B:
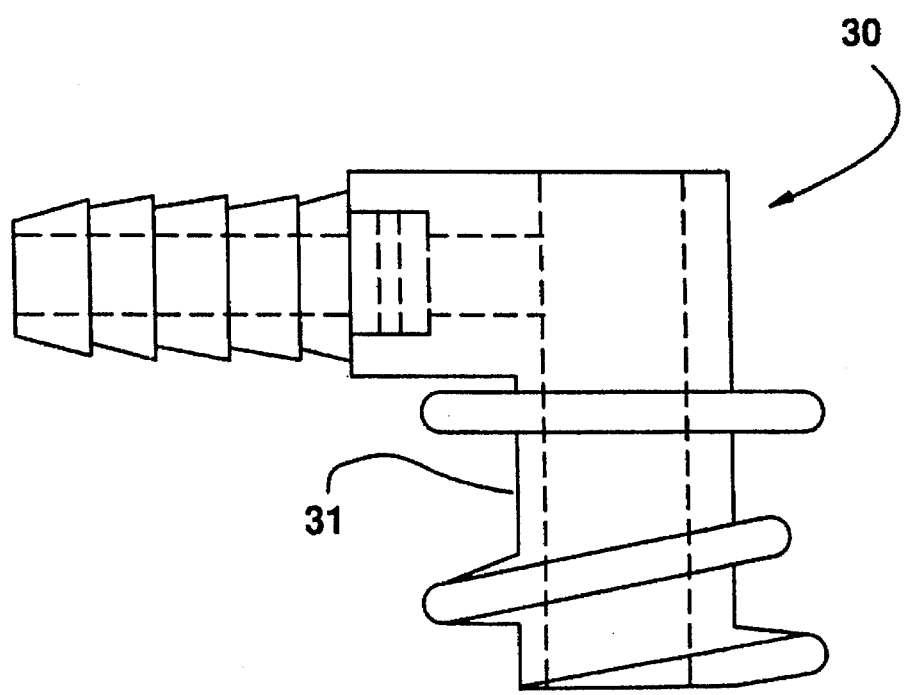
FIG. 2B is a plan view on the skin protector of FIG. 2A.

Referring now to the drawing wherein like reference numerals are used throughout the various views to designate like parts, the skin protector generally designated by reference numeral 30 includes a lower part 31 of tubular configuration preferably of cylindrical configuration which is separated from the upper part 34 by a flange-like annular part 35, preferably in the form of an annular disk-like part whose lower surface 35' forms an abutment surface is intended to rest on the external surface of the skin. A through-bore 33 extending through the upper part 34, the flange-like part 35 and the lower part 31 defines an axial direction 33'. As the cross-sectional area of the flange-like part 35 at right angle to the axial direction 33' is larger than the cross-sectional area of the lower part 31, also at right angle to the axial direction 33', the lower surface 35' of the flange-like part 35 which is intended to rest on the outer surface of the skin, limits at the same time the insertion depth of the skin protector into the incision. A nipple generally designated by reference numeral 37 is provided with an internal bore 39 which is in communication with the internal bore 36' of the stub-like connecting portion 36 forming part of the upper part 34. The nipple 37, which is provided externally with conventional barbs, is connected with the stub-like connecting portion 36 by way of a conventional swivel joint 38 so as to permit the suction line, which may rest on the skin of the patient, to freely rotate through 360° relative to the skin protector. In order to anchor the lower part in the incision and thereby reduce the likelihood of inadvertent removal of the skin protector during the surgical operation, the lower part 31 is provided with anchoring means which, in the preferred embodiment, includes a rib-like spiral 32 extending about the outer surface of the lower part 31. The rib-like spiral 32 thereby extends from the lower free end of the lower part 31 to a point spaced about 4 mm. from the lower surface 35' of the flange-like part 35, i.e., a distance corresponding approximately to the thickness of the skin consisting of epidermis and dermis so that the rib-like spiral 32 will be located in the area of the subcutaneous tissue.

In lieu of a spirally shaped anchoring means 32 shown in the preferred embodiment, other anchoring means are also within the scope of this invention such as a textured outer surface of the lower part, one or more annular rib-like parts extending about the outer surface of the lower part with the distance of the annular rib-like part closest to the lower surface 35' amounting again to about 4 mm., or non-spirally shaped ribs extending in the more or less axial direction which may be tapered and reach a maximum height in the radial direction about 4 mm. from the lower surface 35'. The free end of the lower part 31 may also be provided with a barb of small dimension whose outer surface increases in the direction toward the surface 35'. Additionally, the flange-like part 35 may also have any other shape, such as a polygonal shape, as long as it provides a lower surface 35' forming an abutment surface to rest on the skin. Furthermore, the upper part 34 may also be made of such size and configuration that its cross-sectional area approaches that of the flange-like part 35 so that the lower end surface adjoining the lower part 31 would then form directly the lower surface 35'. The angle defined by the axis of the bores 39 and 36' need not be at right angle but may also be at an angle different therefrom. Furthermore, in order to enhance the aspiration efficiency of the suction line, a seal in the form of an annular ring may be provided near the upper end of bore 33 within an annular groove provided thereat. By choosing the flexibility of the material of the annular ring as well as its dimensions, it is possible to obtain a viable compromise between desirability of free movement of the probe and efficiency of the aspiration.

Turning now to FIG. 3A, this figure illustrates an introducer member generally designated by reference numeral 40 which includes a lower part 41 provided with a blunt end 42 and an upper handle part 43. The lower part 41 intended to be inserted into the incision to create a tunnel for the insertion of the skin protector has a diametric dimension larger than the bore 33 in the skin protector, preferably larger than the diametric dimensions of the lower part 31. The blunt end 42 may be of hemispherical shape.

FIG. 3B illustrates a driver member generally designated by reference numeral SO which includes an upper handle part 51 and a lower introducer part 52. As shown in FIG. 3B, the driver member 50 is provided with an axially extending cut-out 53 in order to be able to mount the driver member 50 over the stub-like connecting portion 36 of the skin protector until its lower surface 53' abuts at the upper surface 34' of the upper part 34. This cut-out 53 thereby extends in the axial direction and is of such dimension as to accommodate the stub-like connecting portion 36. Moreover, this cut-out 53 is not just an axial cut-out but is provided with a further cut 53' so that when the driver member 50, installed over the skin protector 30 is rotated in the counterclockwise direction, a C-shaped lip is formed whose lower end then extends below the stub-like connecting portion 36 in order to be able to withdraw the skin protector together with the driver member SO in the axial direction while the driver member may be rotated in the counterclockwise direction, i.e., in a direction opposite to the direction of the spiral which assists in inserting the skin protector into the incision when rotating the driver member in the clockwise direction.

Typical dimensions of a preferred embodiment are as follows, the values being in appropriate units, such as millimeters. The overall axial height of the skin protector is 20.3 mm.; the axial height of the lower part 31 is 10 mm.; the diameters of the through-bore 33 is 5.5 mm.; the diameter of the internal bore 39 is 3.0 mm.; the height of the rib-like spiral 32 from the lower part 31 is 3.2 mm.; and the overall length of the nipple 37 to the opposite side of the upper part 34 is 27.5 mm. The overall length of the introducer member 40 is 130.8 mm., and the diameter of the lower part 41 is 8.1 mm. The overall length of the driver member 50 is 102.6 mm., and the diameter of the lower introducer part 52 is 5.4 mm. However, it is understood that these dimensions are merely for purposes of illustration and are not to be considered limitative of the invention as they may be modified as known to those skilled in the art. The body of the skin protector 10 which is made in one piece of plastic material by conventional techniques, is preferably made from gas (ETO) or steam sterilizable material which resists deformation and incorporates an outer configuration to aid in maintaining positioning in situ during the operative procedure.

During surgical procedure, a skin protector is positioned through the skin incision prior to insertion of the probe. The ultrasonic probe is then inserted through the port of entry in the skin protector formed by the through-bore, thus eliminating direct contact between the probe and the incisional site. The port of entry may also have a larger surface area or external diameter to provide additional material for protection of direct contact between the probe and the skin.

The skin protector of this invention can be made small in physical dimensions to advantageously minimize the required length of the incision, and to allow for implantation and use thereof in areas with smaller probes, also in areas of less subcutaneous tissue volume. The vacuum outlet has an integrated locking swivel joint to permit full rotation of the vacuum line during the surgical procedure, yet prevents passive disconnection of the vacuum source. The vacuum line may be connected to a standard operating room supply and suction reservoir or to a portable vacuum source. The barbed outer surface of the nipple is provided to accommodate most standard-sized suction tubing.

Examples of materials demonstrating characteristics of durability include, for example, ultra high molecular weight polyethylene (UHMWPE) and ULTEM®. Parts made of ULTEM® permit standard steam autoclave procedures where desired. Both of these materials resist fragmentation and particulation with direct transverse contact of the ultrasonic probe. However, other materials offering similar characteristics may also be used, including those used for throw-away medical parts. The skin protector 10 is inserted into the skin incision with the aid of the driver 50 turning the part in a clockwise direction and thereby anchoring the skin protector in the subcutaneous tissues by means of the rib-like anchoring spiral. The skin protector 30 may be removed again by using the driver 50 to turn in a counterclockwise direction.

The outer configuration of the skin protector 10 may also include various configurations for maintaining temporary implantation in situ, whereby the anchoring configuration is placed at a distance to the base of the skin protector in order to decrease undue stress on the skin at the incisional site.

While we have shown and described only one embodiment of a skin protector in accordance with this invention, it is understood that the same is not limited thereto but is susceptible of numerous changes and modifications as known to those skilled in the art. For example, the lower part 31 may also be without any anchoring means as described in connection with the preferred embodiment. We therefore do not wish to be limited to the details shown and described herein but intend to cover all such changes and modifications as are encompassed by the scope of the appended claims.

We claim:

1. A skin protector, especially for protecting the skin incision from thermal and frictional abrasion during ultrasonic-assisted liposuction, comprising a skin protector body including first means forming a lower part for insertion into the incisions and second means forming an upper part intended to remain external of the skin and including limiting means for limiting the insertion depth of the skin protector into the incision, said body being provided with a substantially aligned through-bore defining an axial direction, and connecting means enabling connection of said through-bore with a suction line, said connecting means extending at an angle to said axial direction from said second means and being provided with a connecting bore angularly disposed to said axial direction and in communication with said through-bore, and said aligned through-bore having a diametric dimension sufficiently large to receive an ultrasonic probe.

2. A skin protector according to claim 1, wherein said limiting means includes a surface means expected to face the skin and having a cross-sectional area larger than the cross-sectional area through said lower part at a substantially right angle to the axial direction.

3. A skin protector according to claim 2, wherein said upper part has a lower end surface, and wherein said surface means is formed directly on the upper part by the lower end surface thereof.

4. A skin protector according to claim 2, wherein said surface means is formed by an annular disk-like part between said upper and lower parts.

5. A skin protector according to claim 1, wherein said skin protector further comprises anchoring means for lessening the likelihood of an unintentional withdrawal of the skin protector out of the incision.

6. A skin protector according to claim 5, wherein said anchoring means is formed by a textured outer surface of the lower part.

7. A skin protector according to claim 5, wherein said lower part has an outer surface, and a free end and wherein said anchoring means includes at least one rib-like means provided over at least a portion of the outer surface of the lower part.

8. A skin protector according to claim 7, wherein said rib-like means is spaced from said limiting means by a distance corresponding approximately to the thickness of the skin consisting of the epidermis and dermis.

9. A skin protector according to claim 7, wherein said rib-like means is spirally shaped commencing in the area of the free end of the lower part and spirally extending about said lower part in the direction toward the upper part.

10. A skin protector according to claim 9, wherein said spirally shaped rib-like means terminates at a distance from said limiting means corresponding approximately to the thickness of the skin consisting of epidermis and dermis.

11. A skin protector according to claim 1, wherein said connecting means includes a nipple connected to said upper part by a swivel joint.

12. A skin protector according to claim 11, wherein said upper part has a stub-like connecting portion of cylindrical shape which forms internally part of the swivel joint.

13. A skin protector according to claim 1, wherein said lower part is of cylindrical shape.

14. A skin protector according to claim 1, wherein said upper part is one of cylindrical and polygonal shape in cross section transverse to the axial direction.

15. A skin protector according to claim 1, wherein the upper and lower parts of said skin protector body as well as the connecting means are made from an autoclavable plastic material.

16. A skin protector according to claim 1, wherein said upper part includes a stub-like connecting portion, and wherein said connecting means includes a nipple operable to be connected to said stub-like connecting portion of the upper part by a swivel joint, said limiting means including an annular disk-like part between said upper and lower parts, and wherein said skin protector is made of an autoclavable plastic material.

17. A skin protector according to claim 16, wherein said skin protector further comprises anchoring means for lessening the likelihood of an unintentional withdrawal of the skin protector out of the incision.

18. A skin protector according to claim 17, wherein said anchoring means is formed by a textured outer surface of the lower part.

19. A skin protector according to claim 17, wherein the lower part has an outer surface and said anchoring means is formed by one of a rib-like means extending about at least a part of the outer surface of the lower part or a textured surface on at least a part of the outer surface of the lower part.

20. A skin protector according to claim 19, wherein said rib-like means is spaced from said limiting means by a distance corresponding approximately to the thickness of the skin consisting of the epidermis and dermis.

21. A skin protector according to claim 19, wherein said rib-like means is spirally shaped commencing in the area of the free end of the lower part and spirally extending about said lower part in the direction toward the upper part.

* * * * *